United States Patent [19]

Ilizarov

[11] Patent Number: 4,978,347
[45] Date of Patent: Dec. 18, 1990

[54] DISTRACTION APPARATUS FOR OSTEOSYNTHESIS OF SHORT TUBULAR BONES

[76] Inventor: Gavrill A. Ilizarov, ulitsa Klimova, 41, kv. 38, Kurgan, U.S.S.R.

[21] Appl. No.: 490,628
[22] PCT Filed: Jul. 26, 1988
[86] PCT No.: PCT/SU88/00152
§ 371 Date: Mar. 20, 1990
§ 102(e) Date: Mar. 20, 1990
[87] PCT Pub. No.: WO90/00883
PCT Pub. Date: Feb. 8, 1990
[51] Int. Cl.[5] .................................. A61F 5/04
[52] U.S. Cl. ........................ 606/54; 606/57; 606/59; 606/105
[58] Field of Search .................... 606/53-59, 606/105

[56] References Cited

U.S. PATENT DOCUMENTS

| | | | |
|---|---|---|---|
| 2,406,987 | 9/1946 | Anderson | 606/56 |
| 3,941,123 | 3/1976 | Volkov | 606/55 |
| 3,977,397 | 8/1976 | Kalnberz | 606/56 |
| 3,985,127 | 10/1976 | Volkov | 606/55 |
| 4,185,623 | 1/1980 | Volkov | 606/55 |
| 4,273,116 | 6/1981 | Chiquet | 606/54 |
| 4,365,624 | 12/1982 | Jaquet | 606/56 |
| 4,554,915 | 11/1985 | Brumfield | 606/54 |
| 4,624,249 | 11/1986 | Alvarez Cambres | 606/54 |
| 4,889,111 | 12/1989 | Ben-Dov | 606/54 |

FOREIGN PATENT DOCUMENTS 2559380 1/1985 France .
1189444 7/1985 U.S.S.R. .
1377078 2/1988 U.S.S.R. .
1424822 9/1988 U.S.S.R. .

OTHER PUBLICATIONS

Orthopedics, Traumatology and Prosthesis Application, No. 7, 1985, Moscow, "Surgical Treatment of Congenital Development Defects and Acquired Deformities of the Hand in Children Using Distraction Techniques," by A. P. Tiazhelkov, pp. 30-32.

Primary Examiner—Robert A. Hafer
Assistant Examiner—Michael Brown
Attorney, Agent, or Firm—Lilling and Lilling

[57] ABSTRACT

In a distraction apparatus for osteosynthesis of short tubular bones, including a support unit (1) made as a cramp-shaped plate (3) having a plurality of perforations (4), two fixing pins (10) being secured between the arms of the cramp-shaped plate (3); distraction units (2) incorporating a pin holder (18) and at least two distraction pins (19) installed therein, a distraction threaded rods (15) whose proximal ends are connected to the support unit (1), according to the invention, the fixing pins (10) of the support unit (1) are arranged parallel to each other and lie in a plane square with the planes of the cramp-shaped plate (3), and each of the distraction units (2) is installed on one distraction rod (15) with a possibility of relative motion along its longitudinal axis, while each of the distraction threaded rods (15) is located on the cramp-shaped plate (3) with a possibility of angular motion and the distraction pins (19) of each distraction unit (2) are cantileverly fixed in the pin holder (18).

6 Claims, 3 Drawing Sheets

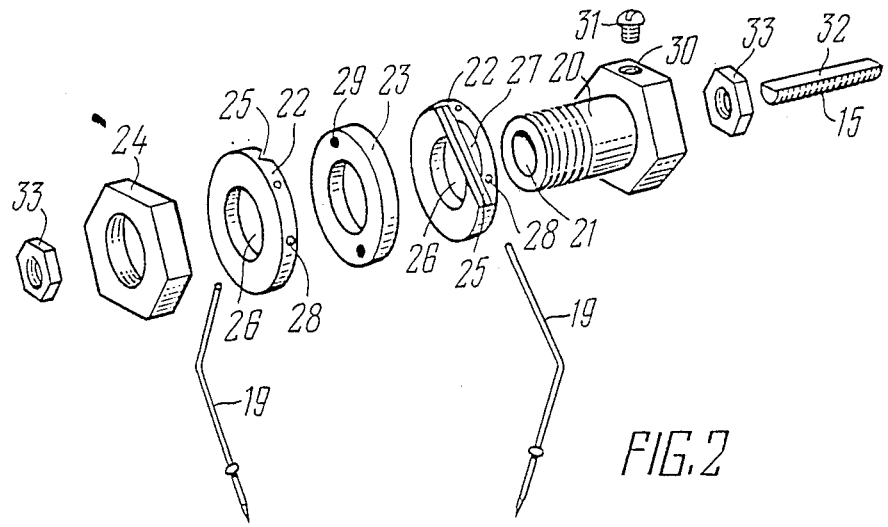
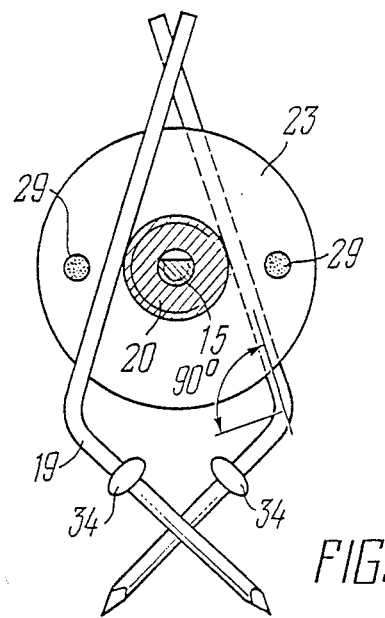 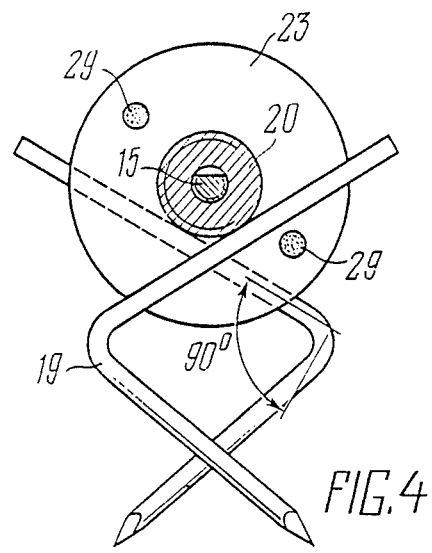

DISTRACTION APPARATUS FOR OSTEOSYNTHESIS OF SHORT TUBULAR BONES

FIELD OF THE ART

The invention relates generally to medical engineering used in orthopedics and traumatology and more specifically, to distraction apparatus for osteosynthesis of short tubular bones.

PRIOR ART

Human hand plays an immense part in man's activities due to its ability to perform complicated and diversified functions. Being the organ engaged in man's labour activities the hand is most frequently liable to sustain traumatic lesions both occupational and domestic, as well as various diseases.

There has been observed a considerable increase in the number of congenital malformations of the hand and foot resulting from administration of sedatives within the initial gestation period. This in turn has promoted considerable progress in the development of surgery of the hand. However, despite the advantages attained in development of external fixation apparatus for short tubular bones, light pathology of the hand still remains one of the most sophisticated problems of present-day traumatology and orthopedics. The aforesaid difficulties stem from the fact that the majority of fixation appliances are aimed at solving the problem of treatment alone, whereas success of treatment is most frequently dependent on a possibility of attaining multiple aims with the aid of a fixation apparatus.

One prior-art orthopedic device for bone fixation (FR, A 2,559,380) is known to comprise a rigid plate carrying two clamps holding fixation pins, each of the clamps comprising two grips which can be interconnected through screws, while at least one of the clamps is movable lengthwise the plate axis. Such a construction arrangement of the clamps enables fixation of each bone fraction separately and makes it possible to stretch out the bone by moving one of the clamps along the plate. However, it should be noted that such a displacement of the bone fragments is insufficiently graduated and cannot therefore assure a required displacement length and rate. In addition, some difficulties arise whenever it becomes necessary to simultaneously stretch out two or more metacarpal bones or digital phalanges.

One state-of-the-art framework for bone fixation (U.S., A, 4,554,915) is known to comprise control members for adjustment of arms in length. An open slot is provided in the other end of the arms adapted to receive a pin connectable to a corresponding bone section. Appropriate members are provided for rigid interconnection of the pins and arms. The fixing unit incorporates also connecting members to join said unit with a second row of pins which are connected to the other bone section on the other side of the fracture.

The aforesaid bone fixation framework is applicable for immobilization in cases of simple diaphyseal fractures of short tubular bones, since it ensures immobilization of bone fragments only on the opposite sides of the fractured bone but cannot be used for stretching-out the metacarpal bones, digital phalanges, or correct their deformaties.

Widely differing from the aforediscussed appliances is the construction of a distraction apparatus for children's hand (cf. Orthopedics, traumatology and prosthesis application, No. 7, 1985, Moscow, 'Surgical treatment of congenital developmental defects and acquired deformities of the hand in children using distraction techniques', by A. P. Tiazhelkov, pp. 30–32 (in Russian). The distraction apparatus comprises a support unit shaped as a cramp-like plate provided with through holes, two fixing pins secured between the arms of said plate, distraction units provided with distraction pins, made similarly to the support unit and positioned in parallel thereto, and distraction threaded rods passing through the open-end holes in the cramp-like plates to interconnect the latter. Pairs of the pins are coplanar with the respective cramp-like plates so as to pass through the bones in the dorsopalmar direction when the apparatus is positioned on the hand.

However, clinical trials have shown that passing of the pins in the dorsopalmar direction and their bringing out on the palmar aspect result in traumatic lesion of the tendons and their sheaths, which is in turn fraught with a variety of secondary morbid states. In addition, the construction under discussion fails to provide a possibility of independent control of the rate and length of stretching-out for each metacarpal bone.

DISCLOSURE OF THE INVENTION

It is a primary and essential object of the present invention to provide a distraction apparatus for osteosynthesis of short tubular bones whose construction would make it possible to separately control the rate and length of stretching-out for each metacarpal bone and to avoid injury to the tendons.

The aforesaid object is accomplished due to the fact that in a distraction apparatus for osteosynthesis of short tubular bones, comprising a support unit made as a cramp-shaped plate provided with a number of perforations and with two fixing pins secured in between the arms of the cramp-shaped plate, distraction units comprising a pin holder and at least two distraction pins installed in said holder, said distraction threaded rods whose proximal ends are connected to the support unit, according to the invention, the fixing pins of the support unit are arranged parallel to each other and lie in a plane square with the planes of the cramp-shaped plate, while each of the distraction units is located on one of the distraction rods with a possibility of relative motion lengthwise its longitudinal axis, each of the distraction threaded rods being situated on the cramp-shaped plate with a possibility of angular motion, and the distraction pins of each distraction unit are cantileverly fixed in the pin holder.

It is expedient that the distraction pins secured on the distraction unit pin holder be curved and their free arms be arranged in a criss-cross manner.

Such a positioning of the pins provides for their stable interaction with the bone fragments through the treatment course.

It is also expedient that the arms of the distraction pins made fast in the pin holder be arranged in a criss-cross manner.

This features adds to faster and more convenient assembly and to rigidity of fastening.

It is possible that the pin holder of the distraction unit be made as a bolt with a nut, both being adapted to fix in position washers fitted on the bolt, the face surfaces of said washers having open slots for the distraction pins to be received therein said open slots passing along the circumferential chord of the washers on the far side of their hole, while the bolt has an axial hole for the distraction threaded rod to pass, said rod having two nuts located on either side of said bolt.

Such a construction arrangement of the pin holder makes it possible to fix the crossed-over distraction pins at a minimum distance from the soft tissues, to conveniently manipulate the pin holder in the course of treatment and to considerably reduce the weight of the distraction unit.

In an alternative embodiment of the invention the distraction apparatus for osteosynthesis of the short tubular bones incorporates an expanding threaded rod whose ends are located on the extreme distraction threaded rods with a possibility of relative motion.

Such a construction arrangement of the distraction apparatus enables one to carry out simultaneously the stretching-out of the metacarpal bones and a uniform widening of the soft tissues in the interdigital spaces for further formation of the digits.

It is practicable that the apparatus, according to one of the embodiments of the invention, be provided with an extra-expanding threaded rod whose ends are located on the middle distraction threaded rods with a possibility of relative motion.

Provision of such an additional expanding threaded rod enables a uniform widening of the soft tissues in the intermetacarpal spaces of the 2nd, 3rd, 4th and 5th metacarpal bones.

SUMMARY OF THE DRAWINGS

In what follows the distraction apparatus for osteosynthesis of short tubular bones is illustrated by some specific exemplary embodiments thereof with reference to the accompanying drawings, wherein:

FIG. 2 is an exploded view of a pin holder of the distraction unit of the apparatus of FIG. 1, according to the invention;

FIG. 3 illustrates the arms of the distraction unit pins of the apparatus of FIG. 1, curved at an obtuse angle, according to the invention;

FIG. 4 depicts the arms of the distraction unit pins of the apparatus of FIG. 1, curved at an acute angle, according to the invention.

PREFERRED EMBODIMENTS OF THE INVENTION

Figure 1:
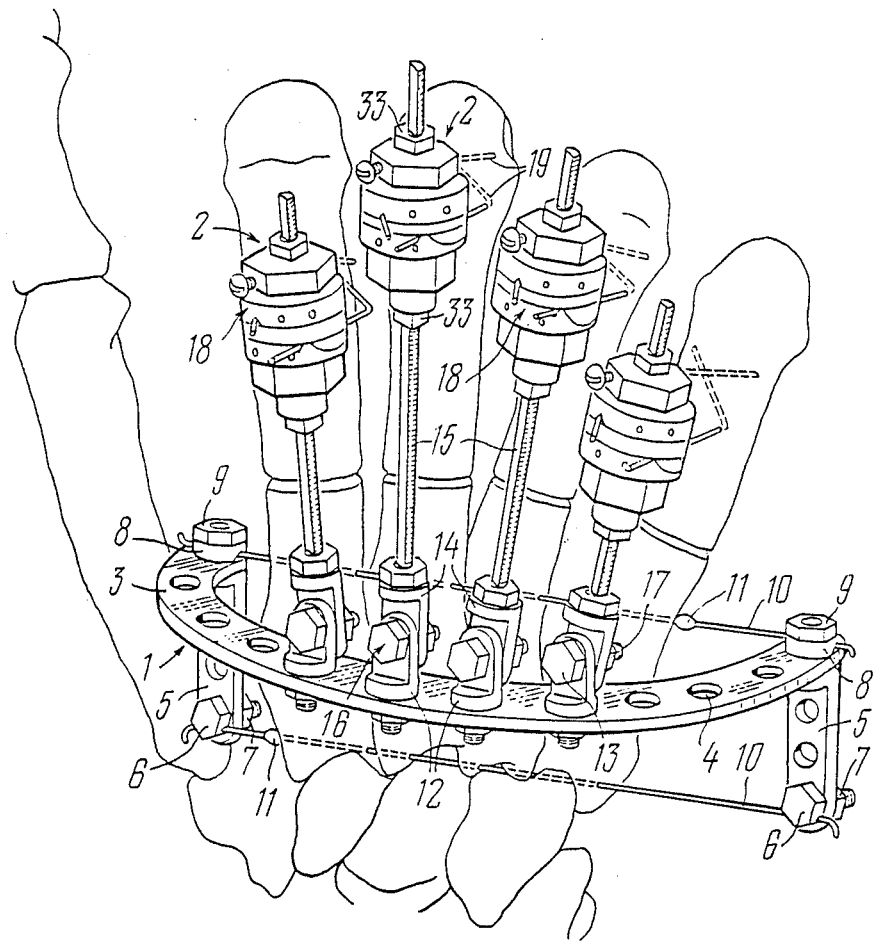
FIG. 1 is a general view of a distraction apparatus for osteosynthesis of short tubular bones, according to the invention, when placed on the metacarpal bones.

The distraction apparatus for osteosynthesis of short tubular bones, according to the invention, comprises a support unit 1 (FIG. 1) and distraction units 2. The support unit 1 incorporates a cramp-shaped plate 3 having a number of perforations 4. Fixing pins 10 having stops 11 are secured at the ends of the cramp-shaped plate 3 with the aid of brackets 5, bolts 6, nuts 7, washers 8 and nuts 9. The fixing pins 10 are arranged parallel to each other and lie in a plane square with the planes of the cramp-shaped plate 3. Brackets 12 are fitted in the perforations 4 of the middle portion of the cramp-shaped plate 3, to which brackets distraction threaded rods 15 are articulated with the aid of bolts 13 and brackets 14. It is due to the brackets 12, 14 and their interconnecting bolt 13 which form an articulated joint 16, that the distraction rods 15 can perform angular motion with respect to the cramp-shaped plate 3. The nuts fitted on the bolts 13 are capable of locking the articulated joint 16 and hence the distraction threaded points 15 in a required position.

Fitted on the distraction threaded rods 15 and longitudinally movavable are the distraction units 2, which incorporate a pin holder 18 and two distraction pins 19. The pin holder 18 of the distraction unit 2 is made as a bolt 20 (FIG. 2) having an axial hole 21 to receive the distraction threaded rod 15, and washers 22 fitted on the bolt 20 and interlaid with a spacer 23. A nut 24 is provided to lock the washers 22 in place. Open slots 25 are provided on the face surfaces of the washers 22 to receive the distraction pins 19, said slots passing along a circumferential chord of the washer 22 on the far side of its hole 26. The washer 22 has a guide flat 27 whose plane is inclined with respect to the face of the washer 22 and is parallel to the longitudinal axis of the open slot 25. Recesses 28 are provided on the cylindrical surface of the washers 22. The spacer 23 is also shaped as a washer, its face surfaces having perforations for magnets 29 to be accommodated therein.

A threaded hole 30 is provided in the head of the bolt 20 square with the axial hole 21 to receive a stop screw 31, which is adapted to interact with a longitudinal flat 32 of the distraction threaded rod 15. The bolt 30 is fixable on the distraction threaded rod 15, as well as movable therealong with the aid of nuts 33.

The distraction pins 19 are curved at an obtuse angle (FIG. 3) or at an acute angle (FIG. 4) and are fitted in the open slots 25 in such a manner that their respective arms are crossed over. Stops 34 (FIGS. 2, 3) may be provided on the free arms of the distraction pins 19 to restrict the depth of penetration of the distraction pins 19 into the bone.

Figure 5:
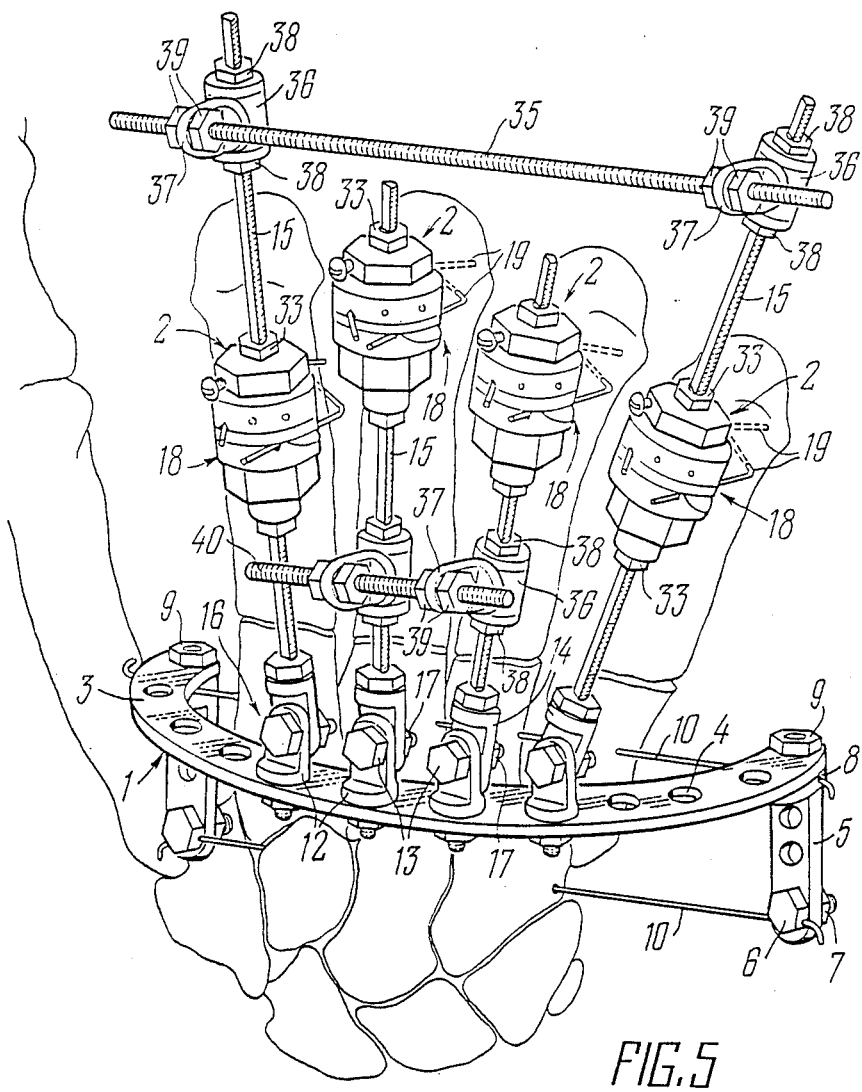
FIG. 5 shows an embodiment of the distraction apparatus for osteosynthesis of short tubular bones, provided with expanding threaded rods, according to the invention.

According to the embodiment of the invention presented in FIG. 5 the distraction apparatus for osteosynthesis of short tubular bones of the present invention comprises an expanding threaded rod 35 located at the distal ends of the extreme distraction threaded rods 15 with the aid of movably interconnected brackets 36, 37 which are situated on the respective extreme distraction threaded rods 15 and at the ends of the expanding threaded rods 35. The brackets 36, 37 are locked in position on the respective threaded rods 15 and 35 and are also traversable therealong with the aid of respective nuts 38 and 39.

An additional expanded threaded rod 40 is interposed between the support unit 1 and the distraction units 2 on the middle distraction threaded rods 15 in a way similar to that described above.

The distraction apparatus for osteosynthesis of short tubular bones according to the invention, as illustrated in FIG. 1 operates as follows.

In order to place the support unit 1, one fixing pin 10 with the stop 11 is passed transversely through the second row of the metacarpal bones and through the bases of the 2nd, 3rd, 4th and 5th metacarpal bones, so that the stops 11 of the fixing pins 10 should be arranged at the opposite sides of the carpus. Then the cramp-shaped plate 3 is fixed at the ends of the fixing pins 10 with the aid of the brackets 5, the bolts 6 with the nuts 7, and the nuts 9 with the washers 8.

The distinction pins 19 are passed pairwise from the dorsal aspect of the wrist through the distal portions of the 2nd, 3rd, 4th and 5th metacarpal bones, whereupon the ends of said pins are crossed over in the bulk of the bone without appearing through the skin on the palmar aspect. Next the pin holders 18 are assembled, comprising the bolt 20, the washers 22 with the spacer 23, leaving a clearance therebetween. Thereupon the nut is loosely fitted on the bolt 20.

Then the pins 19 are bent to make the free arms thereof cross over, and the crossed-over arms are fitted into the slots 25 of the washers 22 with the aid of the guide flat 27 which is preliminarily oriented with respect to the distraction pin 19 by rotating the washer 22 around the bolt 20 using a pointed object such as a needle, by inserting into the recesses 28. It is due to the action of the magnets 29 located in the spacer 23 that the latter covers the open slot 25, thereby keeping the distraction pins 19 in the slots 25 in a required position until the pins 19 are rigidly fixed in the pin holder 18 by drawing the nut 24 tight.

Next the pin holders 18 with the distraction pins 19 are placed on the distraction threaded rods 15, which are linked, through the brackets 14, 12 interconnected through the bolt 13 and the nut 17, to the cramp-shaped plate 3. In this case the direction of the distraction threaded rods 15 should coincide with the direction of the longitudinal axis of the metacarpal bones. Thereafter the distraction threaded rods 15 are dismantles, small incisions are made in the intermetacarpal spaces, osteotomy of the 2nd, 3rd, 4th, and 5th metacarpal bones is carried out, the distraction threaded rods 15 are reinstalled, and the apparatus are assembled. Then the distraction process commences, aimed at stretching-out the bones by gradual tightening of the nuts 33 at a preset rate and pace.

The distraction apparatus for osteosynthesis of short tubular bones according to an embodiment of the invention presented in FIG. 5, is applicable for distraction of the metacarpal bones towards their longitudinal axis, accompanied by stretching-out and extension of the soft tissues in the interdigital space in the following manner.

The distal fixing pin 10 is passed through the proximal portion of the metacarpal bones, while the proximal fixing pin 10 is passed parallel to the distal one through a second row of the metacarpal bones, whereupon both of the pins are fixed in the support unit 1. A pair of the crossing-over pins 19 is passed through the distal portions of the metacarpal bones from the dorsal aspect, whereupon the pins are cantileverly clamped in the pin holders 18. Then the latter are connected to the cramp-shaped plate 3 with the aid of the distraction threaded rods 15 and the brackets 14, 12 interconnected through the bolt 13 and the nut 17. Next the expanding threaded rod 35 is fitted over the extreme distraction threaded rods 15 using the bracket 37, while the additional expanding threaded rod 40 is fitted over the middle distraction threaded rods 15 using the bracket 36.

Thereupon the expanding threaded rods 35, 40 and the distraction threaded rods 15 are dismantled. Osteotomy of the metacarpal bones is carried out through skin incisions made beforehand in the metacarpal spaces, the distraction threaded rods 15 are reinstalled, as well as the expanding threaded rods 35, 40, thereby connecting the distraction units 2 to the support unit 1. When interconnected the brackets 14, 12 establish the articulated joint 16 having a pivot pin in the form of the bolt 13, aligning with the pivot axis of the metacarpal bones in the front plane of the carpometacarpal joint. Making use of said articulated joint one should orient the distraction threaded rods 15 in the direction of the divergent radii of the metacarpal bones, whereupon stretching-out of the metacarpal bones is carried out by gradually tightening the nuts 33 on the distraction threaded rods 15, while gradual extension of the intermetacarpal spaces is carried out by tightening the nuts 39, i.e., the stock of the soft tissues is grown up for further formation of the fingers.

The construction of the apparatus, according to the invention, enables one to assemble a required construction arrangement of the apparatus quickly and simply, using a minimum range of its component parts. The function of the apparatus is easily and conveniently variable to suit the specific features of a treatment course with due account of biomechanical requirements, which makes it possible to attain favourable clinical results. Simple assembly, guaranteed low degree of traumatism, small overall dimensions and highly reliable fixation, all this makes the instrument applicable by a wise range of specialists.

INDUSTRIAL APPLICABILITY

The invention can find most utility when applied for treatment of pathological conditions of the hand and foot accompanied by partial loss of the segment, its underdevelopment or deformation, as well as for treatment of deformations and defects of the traumatic origin. The apparatus provides for optimum conditions for simultaneous restoration of the anatomic structures and function of both the hand and foot. Making use of the present distraction apparatus for osteosynthesis of short tubular bones by the closed method, as well as in combination with diverse operative techniques one can grow up fingers from the metacarpal bones, resposition bone fragments by growing the osseous tissue in the case of a periarticular on diaphyseal fracture, or correct a wrong bone position in the case of ankylosis.

What is claimed is:

1. A distraction apparatus for osteosynthesis of short tubular bones, comprising a support unit (1) made as a cramp-shaped plate (3) provided with a plurality of perforations (4) and with two fixing pins (10) secured in between arms of the cramp-shaped plate, distraction units (2) comprising a pin holder (18) and at least two distraction pins (19) installed in said holder, and distraction threaded rods (15) whose proximal ends are connected to the support unit (1), characterized in that the fixing pins (10) of the support unit (1) are arranged parallel to each other and lie in a plane square with the planes of the cramp-shaped plate (3), while each of the distraction units (2) is located on one of the distraction rods (15) with a possibility of relative motion lengthwise its longitudinal axis, each of the distraction threaded rods (15) being situated on the cramp-shaped plate (3) with a possibility of angular motion, and the distraction pins (19) of each distraction unit (2) are cantileverly fixed in the pin holder.

2. An apparatus as claimed in claim 1, characterized in that the distraction pins (19) secured on the distraction unit pin holder (18) are curved and their free arms are arranged in a criss-cross manner.

3. An apparatus as claimed in claim 2, characterized in that the arms of the distraction pins (19) made fast in the pin holder (18) are arranged in a criss-cross manner.

4. An apparatus as claimed in claim 3, characterized in that the pin holder (18) of the distraction unit (2) is made as a bolt (20) with a nut (24) both being adapted to fix in position washers (22) fitted on the bolt (20), the face surfaces of said washers having open slots (25) for the distraction pins (19) to be received therein, said open slots (25) passing along the circumferential chord of the washers (22) on the far side of their hole (26), while the bolt (20) has an axial bore (21) for the distraction threaded rod (15) to pass, said rod having two nuts (23) each being located on one side of said bolt (20).

5. An apparatus as claimed in claim 1, characterized in that it incorporates an expanding threaded rod (35) whose ends are located on the extreme distraction threaded rods (15) with a possibility of relative motion.

6. An apparatus as claimed in claim 5, characterized in that it has an additional expanding threaded rod (40) whose ends are located on the distraction threaded rods (15) with a possibility of relative motion.

* * * * *